United States Patent [19]

Ashley et al.

[11] Patent Number: 5,762,945
[45] Date of Patent: Jun. 9, 1998

[54] COMPOSITION AND METHOD FOR TREATING DIAPER RASH

[76] Inventors: Paul Ashley, deceased, late of Crete, Ill.; by Eline Ashley, executrix, 3639 Beckwith La., Crete, Ill. 60417-1260

[21] Appl. No.: 628,776

[22] Filed: Apr. 5, 1996

[51] Int. Cl.[6] .................................................. A61K 7/48
[52] U.S. Cl. ........................... 424/401; 424/642; 514/865
[58] Field of Search ................................. 424/401, 642; 514/805

[56] References Cited

U.S. PATENT DOCUMENTS

| | | | |
|---|---|---|---|
| 3,567,820 | 3/1971 | Sperti | 424/79 |
| 4,996,238 | 2/1991 | Matravers | 514/865 |
| 5,091,193 | 2/1992 | Enjolas et al. | 424/642 |
| 5,362,488 | 11/1994 | Sibley et al. | 424/78.05 |
| 5,409,903 | 4/1995 | Polak et al. | 514/23 |

*Primary Examiner*—Jyothsna Venkat
*Attorney, Agent, or Firm*—David L. Volk

[57] ABSTRACT

A topical composition for the treatment of the symptoms of diaper rash is disclosed comprising the combination of equal rations of nystatin powder, zinc oxide, and AQUAPHOR (™), and mixed with a larger volume of U.S.P. cold cream.

5 Claims, No Drawings

COMPOSITION AND METHOD FOR TREATING DIAPER RASH

BACKGROUND OF THE INVENTION

1. Field of the Invention

The present invention relates generally to topical compositions used in the treatment of a skin condition commonly known as "diaper rash" and, more particularly, to a topical composition containing nystatin power as an active ingredient in the killing of yeast and bacteria. The present invention also relates to a method for treating diaper rash by the topical use of a composition containing nystatin powder as an active ingredient.

2. Description of the Related Art

A skin condition commonly known as "diaper rash" is prevalent among infants everywhere. Generally associated as a result of increased bacteria and yeast activity, many methods of topically alleviating the irritation caused by such rashes are generally known. Currently, the most popular over-the-counter remedies attempt to block irritations by repelling moisture by forming a greasy barrier, but fail to provide any active yeast or bacterial killing abilities. Such an example is also disclosed in U.S. Pat. No. 4,996,238, issued in the name of Matravers.

Another commonly used active ingredient includes zinc oxide. Typical of such a product is disclosed in U.S. Pat. No. 5,091,193, issued in the name of Enjolras et al.

Other remedies for alleviating skin irritations are also known which attempt 5 to absorb excess ammonia and ammonium irritants. An example is disclosed in U.S. Pat. No. 3,567,820, issued in the name of Sperti. Similarly, pH control is also used in an attempt to limit irritation, an example of which is disclosed in U.S. Pat. No. 5,362,488, issued in the name of Sibley et al.

Consequently, a need has been felt for providing a composition and method for treating diaper rashes which can actively eliminate bacteria and yeast generated irritations.

SUMMARY OF THE INVENTION

It is therefore an object of the present invention to provide an improved composition for treating diaper rash.

It is yet another object of the present invention to provide an improved composition for treating diaper rashes which include yeast or bacteria-based irritations.

It is a feature of the present invention to provide a novel use for a topical preparation containing nystatin power in combination with zinc oxide and aquaphor.

Briefly described according to one embodiment of the present invention, a new topical composition for the treatment of diaper rashes is provided which comprises a combination of nystatin power, zinc oxide, AQUAPHOR (™), and U.S.P. cold cream. Also provided is a new method for treating diaper rashes which comprises administering an effective amount of the aforementioned combination directly to inflamed areas of the skin.

Advantages of the present invention are that is easily applied, rinses off cleanly, is easy and inexpensive to manufacture, and is effective by itself or in combination with other conventional treatments.

DESCRIPTION OF THE PREFERRED EMBODIMENTS

It has now been discovered that a topical application of a combination of nystatin powder, zinc oxide, and aquaphor, all carried in a carrier diluent of U.S.P. cold cream applied directly to an effected area of skin can provide relief from the symptoms of diaper rash. In its preferred embodiment, the combination is made of the following composition: nystatin power—30 mg; zinc oxide—30 mg; AQUAPHOR (™)—30 mg; and U.S.P. cold cream—120 mg. AQUAPHOR (™) is a preparation consisting of petrolatum, mineral oil, ceresin and lanolin alcohol.

It is also currently envisioned that an inert carrier may be added in order to vary the effective concentration of the active ingredients. Also, the composition can also include the addition of fragrance to provide a more pleasant olfactory aesthetic for the user.

The foregoing description is included to illustrate the operation of the preferred embodiment and is not meant to limit the scope of the invention. From the forgoing description, many variations will be apparent to those skilled in the art that would yet be encompassed by the spirit and scope of the invention. Therefore, the scope of the invention is to be limited only by the following claims.

What is claimed is:

1. A composition for topically treating diaper rash consisting essentially of a combination of equal portions of nystatin powder, zinc oxide, and a preparation consisting of petrolatum, mineral oil, ceresin and lanolin alcohol, said combination solvated in a pharmaceutically acceptable diluent, mixed smoothly to a single-phase preparation.

2. The composition for topically treating diaper rash as described in claim 1, wherein said pharmaceutically acceptable diluent is U.S.P. cold cream.

3. A composition for topically treating diaper rash comprising:
   a. 30 mg of nystatin powder;
   b. 30 mg of zinc oxide;
   c. 30 mg of a preparation consisting of petrolatum, mineral oil, lanolin alcohol and ceresin;
   d. 120 mg of U.S.P. cold cream;
   wherein said combination is mixed smoothly to a single-phase preparation.

4. A method, for treating diaper rash, comprising the topical application of a composition consisting essentially of a combination of equal portions of nystatin powder, zinc oxide, and a preparation consisting of petrolatum, mineral oil, ceresin and lanolin alcohol, said combination solvated in a pharmaceutically acceptable diluent, mixed smoothly to a single-phase preparation.

5. The method for topically treating razor burns as described in claim 4, wherein said pharmaceutically acceptable diluent is U.S.P. cold cream.

* * * * *